United States Patent [19]

Vande Ven et al.

[11] 3,973,440
[45] Aug. 10, 1976

[54] CATALYST SAMPLING METHOD

[75] Inventors: John E. Vande Ven, Bensenville, Ill.; Steven M. Fischer, Jacksonville, Fla.

[73] Assignee: Universal Oil Products Company, Des Plaines, Ill.

[22] Filed: Apr. 28, 1975

[21] Appl. No.: 572,603

[52] U.S. Cl. ............................................. 73/421 B
[51] Int. Cl.² .......................................... G01N 1/14
[58] Field of Search .......... 73/421 B, 421 R, 423 R, 73/424

[56] References Cited
UNITED STATES PATENTS

| | | | |
|---|---|---|---|
| 3,129,590 | 4/1964 | Ellis | 73/421 B |
| 3,348,419 | 10/1967 | Addison | 73/424 |
| 3,442,138 | 5/1969 | Hensel | 73/423 R |
| 3,487,695 | 1/1970 | Haunschild | 73/421 B |
| 3,653,265 | 4/1972 | Vallino | 73/421 B |
| 3,786,682 | 1/1974 | Winter | 73/421 B |

*Primary Examiner*—S. Clement Swisher
*Assistant Examiner*—Denis E. Corr
*Attorney, Agent, or Firm*—James R. Hoatson, Jr.; Robert W. Erickson; William H. Page, II

[57] ABSTRACT

Small representative samples of catalyst are removed from a fixed bed reactor through a withdrawal conduit and transferred into a sample receiver held at a lower pressure by quickly unsealing the withdrawal conduit and causing a small and sudden gas flow which fluidizes catalyst and lifts it into the withdrawal conduit, through which it falls by the action of gravity.

3 Claims, 3 Drawing Figures

CATALYST SAMPLING METHOD

FIELD OF THE INVENTION

The invention relates to the field of measuring and testing. It directly relates to solid material samplers, such as used to withdraw catalyst particles from operating reactors or regenerators.

DESCRIPTION OF THE PRIOR ART

The prior art has recognized the importance of obtaining samples of catalyst from within an operating catalytc reactor. This provides useful information on such factors as the amount of coke on the surface of the catalyst, the amount of metals deposited on the catalyst, the halogen content, surface area, platinum crystallite size or oxidation state of the catalyst. One type of sampler developed to supply this information mechanically opens and closes the sampling port located at the end of the probe. This type of sampler is represented by the device shown in U.S. Pat. No. 3,348,419 (Cl. 73-424). In this reference, a hollow withdrawal conduit is rotated within a hollow shaft to open and close an opening into the withdrawal conduit. U.S. Pat. No. 3,442,138 describes a nonrotating shaft which slides in a reciprocating manner within an outer shaft to operate the catalyst outlet. These samplers have several disadvantages which the prior art has recognized. The movement associated with their operation tends to crush catalyst and the mechanical nature of the probe requires close tolerances. The temperature differences experienced by the sampler and the fine particles combine to make operation difficult. It also results in binding and galling of the moving parts.

A second type of sampling device produces or controls the flow of catalyst pneumatically. For instance, in U.S. Pat. No. 3,653,265, the differential pressure between the reaction vessel and a solids receiver is used to create a gas stream which carries catalyst upward and out of the vessel. The rate of catalyst withdrawal is regulated by a flow of purge gas delivered to the inlet of the withdrawal conduit. An increase in the purge gas rate decreases the flow of gas from the vessel and therefore the catalyst transfer. A second system shown in U.S. Pat. No. 3,786,682 delivers a high velocity gas flow to the end of the withdrawal conduit via a small tube contained within the conduit. This high-velocity flow prevents catalyst from entering the tube except for when it is reduced, and the construction allows removal of all catalyst from the conduit. This second type of sampling device removes the mechanical problems, but the required gas flows to remove small amounts of catalyst are difficult to control and measure. The second system also has a second disadvantage in that the high gas rate forms an unrepresentative environment near the catalyst sampling port and therefore tends to produce unrepresentative samples.

U.S. Pat. No. 3,487,695 presents a withdrawal conduit similar in construction to that preferred for use with the subject method. However, the operation used to withdraw catalyst differs. The pressure within the sample receiver is equilibrated with the reactor, and the two volumes are brought into open communication through the withdrawal conduit. The catalyst is then transferred by a gas flow produced by briefly venting the sample receiver to an external point.

BRIEF SUMMARY OF THE INVENTION

Representative catalyst samples are removed from a sampling point within a vessel containing a fixed bed of catalyst in a mechanically simple system without the use of large gas streams. The invention comprises the steps of sealing a withdrawal conduit at a point intermediate the sampling point and a sample receiver, evacuating the sample receiver, and opening the seal in the withdrawal conduit to create a short, sudden rush of gases into a catalyst port in the withdrawal tube, which fluidizes a small quantity of catalyst and carries it upward into the withdrawal conduit. The catalyst then falls to the sample receiver by the action of gravity.

DESCRIPTION OF THE DRAWING

Referring now to FIG. 1, the outer wall 1 encloses a reactor containing a fixed bed of catalyst particles 2. The reactor is shown as it would appear in cross-section when an annular bed of catalyst is used. A cylindrical porous wall 3 of catalyst retaining screen and a porous cylindrical center pipe 4 define the outer extremities of the catalyst bed. The reactants may flow radially in either an inward or outward direction. The catalyst sampling system includes a withdrawal conduit 5 which extends upward into the catalyst bed. A catalyst entrance port 6 is located near the upper end of the withdrawal tube. The withdrawal conduit passes into the reactor through a catalyst removal nozzle which is filled with inert spheres of a larger diameter than the catalyst. Line 9 carries a small stream of a heated purge gas at a rate controlled by valve 10 and delivers the purge gas to the base of the withdrawal conduit. Just below this point is located a valve 8 which can form a pressure tight seal across the withdrawal conduit. A second line 11 connects with the conduit 14 extending downward from the valve. This line may lead to a vacuum source or may be a simple vent line. Line 11 can also supply purge gas to the conduit. The flow through this line is controlled by valve 12. A second valve 15 is provided in the withdrawal conduit below line 11. Either valve 8 or valve 15 may be utilized as the main sealing or surge valve. Two valves are provided as a safety measure. A cylindrical sample receiver 13 is located below valve 15.

FIG. 2 illustrates the preferred construction of the downward facing catalyst entrance port 6, which is located at the upper end of the withdrawal conduit 5, when this conduit is to be mounted on an incline. The entrance port is the unsealed lower end of a small tube 16, which extends within the withdrawal conduit and points upward toward the cap 19 sealing the upper end of the conduit. The upper end 20 of tube 16 will preferably be near horizontal when the conduit is installed.

FIG. 3 represents a summary of experimental data on the relationship of the pressure differential applied between the vessel and the sample receiver to the amount transferred under one specific set of conditions. The data is presented as a band since the amount transferred was found to vary slightly with different configurations of the entrance port and upper portion of the withdrawal conduit. This data was obtained using 1/16-inch reforming catalyst base material with nitrogen as the pressurized gas. The volume of the sample receiver and tubing below the main valve was about 55 cubic inches.

DETAILED DESCRIPTION

Figure 2:
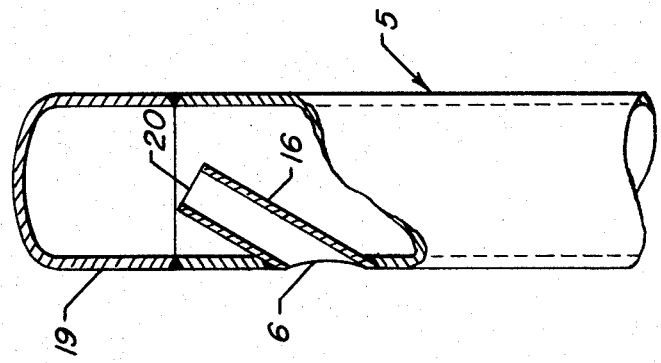
FIG. 2 illustrates the preferred construction of the upper end of catalyst withdrawal conduit when the conduit is inclined during use.
Figure 1:
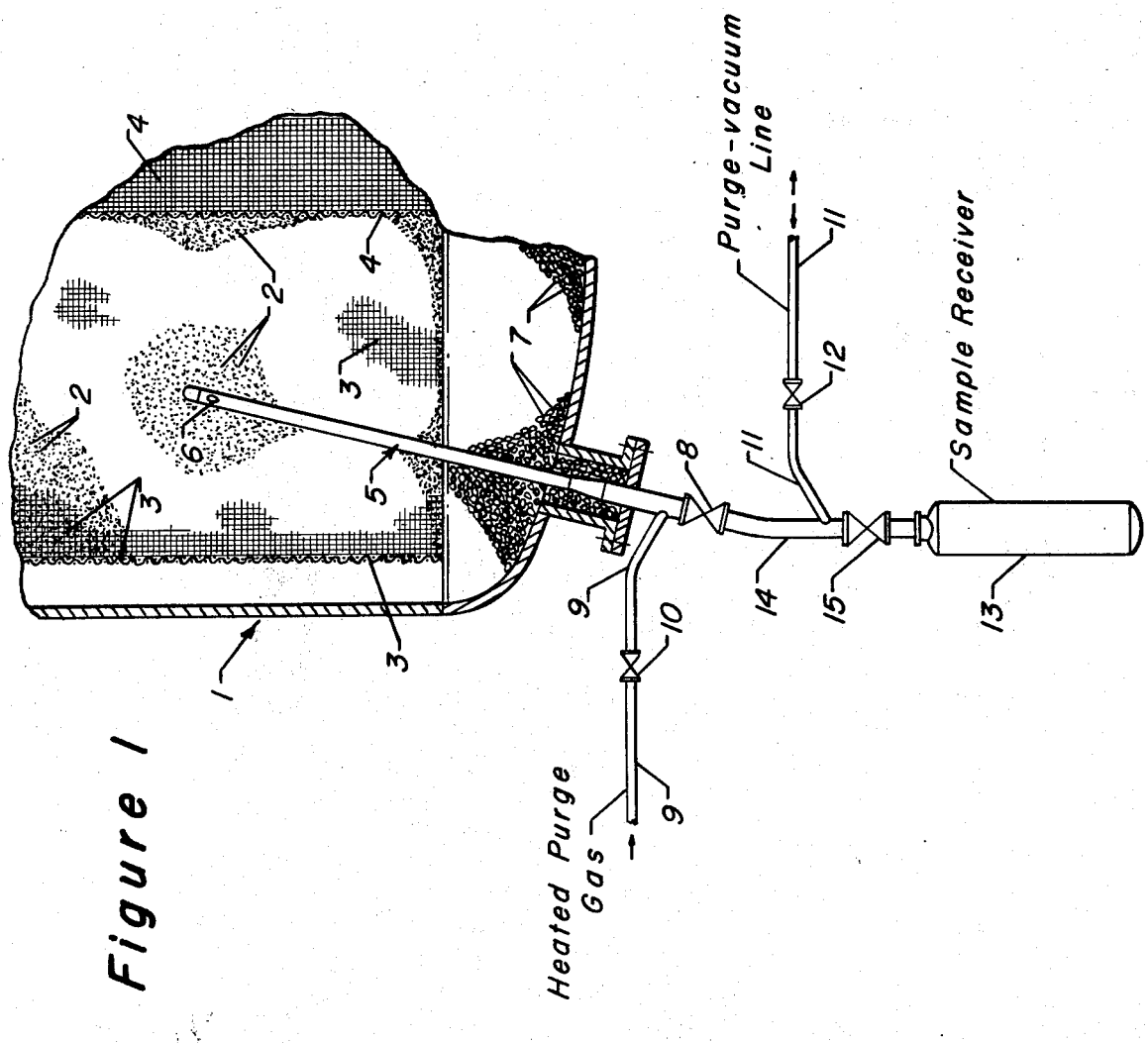
FIG. 1 presents a vertical cross-section of a fixed bed catalytic reactor in which a system adapted to the use of the subject method has been installed.

The prior art has recognized the importance of obtaining samples of catalyst from within an operating reactor and has proceeded in the course set out above to develop first mechanical and then pneumatic systems to remove the desired samples. The pneumatic systems are preferred since they do not require moving parts, which tend to bind after a limited time in operation and to crush catalyst during their operation. It is desired that the pneumatic system does not require a large continuous gas stream during operation as this increases utility costs. The utility costs involved are however secondary in importance to the ability of the system to provide a representative sample. If a gas stream emerges from the point at which the catalyst enters the sampling means, it produces a local environment which is not representative of that generally found within the reactor. This produces misleading results when the catalyst sample is analyzed. It is therefore an objective of this invention to provide a method and system for removing representative catalyst samples from a reactor. It is another objective to provide a pneumatically operated catalyst sampling method which delivers representative samples and has a low rate of gas consumption. A further objective is to provide a sampling system which automatically provides samples containing a small, uniform and controllable amount of catalyst.

These objectives are achieved by producing a sudden but small flow of the gas which fluidizes the desired small quantity of catalyst and carries it in an upward direction into a catalyst withdrawal conduit. The catalyst is then transported downward through the withdrawal conduit by the action of gravity. This small gas flow is produced by first sealing the withdrawal conduit to gas flow at a point between the point in the reactor at which the sample is desired, referred to herein as the sampling point, and the sample receiver. The sample receiver is then evacuated, that is, the pressure in the sample receiver is reduced below that in the reactor. Preferably, pressure differential created in this way is in excess of 20 psig. The obstruction in the withdrawal conduit is then rapidly removed. This produces a sharp pulsed flow of a regulated volume of gas into the area of lower pressure, which flow stops in the short time required for the two pressures to equalize. The volume of the gas flow is controlled by the evacuated volume and the pressure differential used.

In accordance with this description, the invention may be characterized as a method of transferring a catalyst sample from a sampling point within a vessel containing a bed of catalyst into a withdrawal conduit having a downward-facing catalyst entrance port, and of transferring the catalyst sample into a sample receiver located outside of the vessel which comprises the steps of sealing the withdrawal conduit to gas flow at a point intermediate the sampling point and the sample receiver, evacuating the sample receiver and creating a pressure therein lower than that maintained in the vessel, rapidly unsealing the withdrawal conduit and passing a short and rapid gas flow through the withdrawal conduit, which equalizes the pressures within the vessel and the catalyst receiver, and effecting a fluidization of catalyst into the entrance port of the withdrawal conduit and the transfer of catalyst through the withdrawal conduit to the sample receiver.

The subject method has an advantage over the pneumatic systems of the prior art in its ability to automatically regulate the amount of catalyst withdrawn with a good degree of precision. This is an improvement over monitoring the amount withdrawn by such means as a sight glass, which presents a severe safety hazard due to the pressure and thermal shock to which the glass is subjected. The intrinsic control of the quantity of flowing gas ensures that the system will not remove an excessive amount of catalyst, which could fill the withdrawal conduit or lead to loss of the seal at the top of the catalyst bed. The subject method also does not require any time measurements to monitor the amount transferred.

Figure 3:
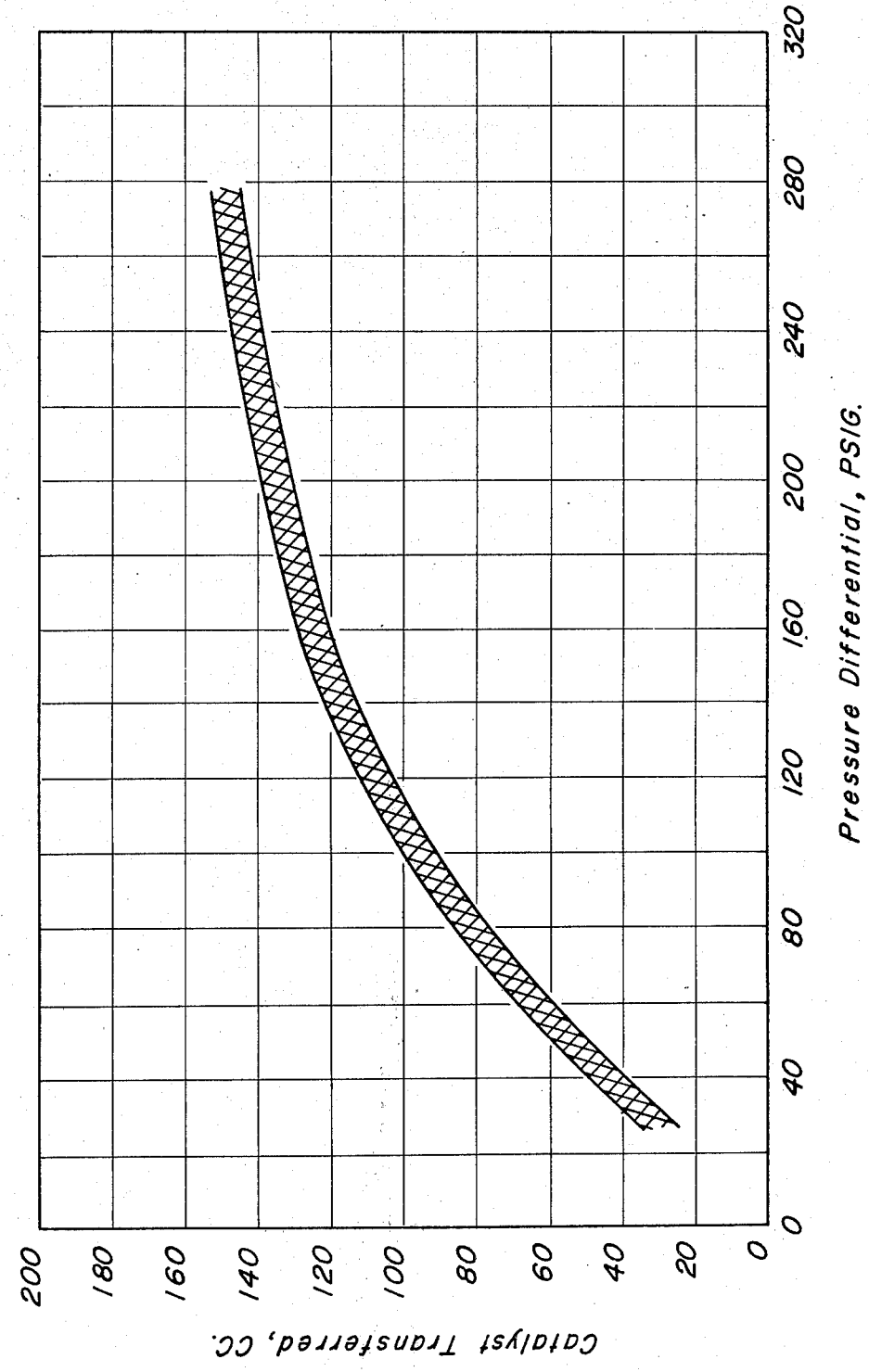
FIG. 3 illustrates the relationship between the pressure differential applied to one specific system and the amount of catalyst transferred.

The amount of catalyst withdrawn is dependent on two variables, the volume of the receiver and conduits below the main seal valve and the pressure differential between this volume and the reactor. Experimental work has determined that the amount of catalyst withdrawn bears a non-linear relationship to the pressure differential between the reactor and the sample receiver. The amount withdrawn can therefore be adjusted in an installed system of unknown volume by changing the pressure differential. The relationship between the pressure differential and the sample obtained is shown in FIG. 3 for one specific set of conditions. The performance of other systems will vary according to the configuration of the withdrawal conduit, type of catalyst sampled, etc. However, the information required to produce a graph similar to FIG. 3 may be obtained with only a few test runs. For a newly installed system, the first sampling should be attempted with a low pressure differential of about 20–30 psig. in order to ensure only a small amount is withdrawn. This amount is measured, and if different than desired, FIG. 3 may be consulted to estimate the pressure differential required. The size of the sample withdrawn should theoretically also bear a linear relationship to the volume of the evacuated part of the system. Varying the size of the receiver may therefore be used as an alternative to adjusting the pressure differential. The size of the sample receiver should be varied if the optimum pressure differential arrived at is either excessive or so small that minor inaccuracies in pressure measurement produce sizable variances in the amount of catalyst withdrawn.

The system may be applied to either fixed or moving beds of catalyst although normally sampling is done only in vessels containing a fixed bed of catalyst. The invention may be used to sample catalyst in vessels other than a reactor or reaction zone. For instance, it may be used to monitor a treatment process or step, such as halogenation, conducted in a regeneration zone or during the production of the catalyst.

Those skilled in the art will recognize other applications to which this method is adaptable and will also realize that mechanical systems for carrying out the process may have a different configuration from that described herein. Experiments have proven the method workable with different configurations for the catalyst entrance port and the upper end of the withdrawal conduit. For instance, the end may be bent to curve downward in a manner similar to the top of a cane, or a cone may be spaced slightly above the open end of the conduit. Other usable configurations are shown in U.S. Pat. No. 3,487,695. The catalyst entrance port must however face downward to prevent catalyst from falling into the withdrawal conduit between samples. It is preferred that the upper end of the conduit has the same outer diameter as the rest of the conduit to allow its easy insertion into and removal from the vessel. The conduit may be inserted through the unloading nozzle usually provided at the bottom of the reactor, and is adaptable for use with either vertical or inclined nozzles. It is especially preferred that the conduit is constructed as shown in FIG. 2. This design satisfies the criterion of holding the dead space in the entrance to the withdrawal conduit to a minimum and thereby ensures a more representative sample.

Since the vessel from which the catalyst is to be removed may be operated at a pressure greatly in excess of atmospheric pressure, the optimum pressure differential may require the sample receiver to also be above atmospheric pressure. The term "evacuating" is therefore used herein in reference to the pressure within the vessel and may require simply bleeding off a portion of the pressurized contents of the receiver or connecting the receiver to a vacuum source. The catalyst should be kept in an inert atmosphere after its removal from the bed. It is therefore preferred that the sample receiver be purged with nitrogen and placed under a positive pressure if possible. There are several reasons for this. First of all, if air is present, an explosive mixture could result and be ignited by hot catalyst. Secondly, the air may cause oxidation of components of the catalyst which are to be analyzed. The amount of coke on the surface of the catalyst could also be affected by either an oxygen or hydrocarbon containing atmosphere.

One step in the process of the invention comprises "isolating" the sample receiver. This is intended to mean a sealing off of the receiver and the conduit between it and the main sealing valve from such external connections as purge or vent lines. In other words, when the sample receiver is isolated, there is no avenue by which reactants may escape. This is a significant difference from those sampling methods which fluidize the catalyst by bleeding off a constant or variable stream of gas from the vessel containing the catalyst bed.

A small continuous stream of heated purge gas is preferably passed into the bottom of the withdrawal conduit at a point just above the main sealing valve. This is to prevent the condensation of hydrocarbons, and the concomitant coke formation, from occurring in the withdrawal conduit. The flow rate of this stream is preferably controlled by a restriction orifice. The purge stream may be shut off during the sampling procedure, but such a small stream is required that it does not interfere with the withdrawal if it is not shut off.

To further illustrate the construction and operation of the invention, a sampler adapted for use on fixed bed radial flow reformers utilizing 1/16-inch nominal spherical catalyst will be described. The withdrawal conduit is formed from a 1-inch schedule 40S pipe which preferably extends upward to a point equidistant the reactor wall and the edge of the centerpipe screen. Samples may of course be obtained with a plurality of samplers to profile catalyst characteristics in the bed. A one-half inch O.D. 16 gauge tube is used to form the catalyst inlet tube to the withdrawal conduit. It is welded to an opening in the conduit at an angle of 30° from the longitudinal axis of the conduit. The conduit is installed with the opening orientated perpendicular to the reactant flow. The top of the withdrawal conduit is sealed with a one-inch weld cap, and the upper end of the 16 gauge tube is centered within the withdrawal conduit. The withdrawal conduit is sealed by means of a 1½-inch stainless steel ball valve with extended bonnet and metal seats. The sample receiver is a 1½-foot long section of 2-inch schedule 80 pipe. This arrangement is suitable to deliver a sample of approximately 100 cc. in volume with the correct pressure differential between the reactor and the sample receiver. The sample receiver itself is provided with a gate valve at each end and a pressure gauge.

The preferred operation of the system comprises first attaching the sample receiver to the withdrawal conduit, with the receiver having first been purged and placed under a slight positive pressure with nitrogen. The upper valve of the receiver and the intermediate or backup valves are then opened. The vent line is closed, and the main valve is then quickly opened to allow a quantity of the reactants to rush into the sample receiver and associated lines. This produces a short pulse of gas flow into the withdrawal conduit, which fluidizes a quantity of catalyst and transfers this quantity into the withdrawal conduit through the catalyst entrance port and upward extending tube. The catalyst is then carried downward by the gas, or it simply falls through the withdrawal conduit and into the sample receiver. The main valve is then closed and the vent line is opened. The vent line is kept open and the second valve just above the sample receiver is closed as a safety precaution. This forces any leakage through the main valve to be vented rather than contact the person removing the sample receiver. The receiver is allowed to cool and is then removed from the withdrawal conduit. At this point, the receiver is depressurized and may be purged with nitrogen if desirable.

We claim as our invention:

1. A method of transferring a catalyst sample from a sampling point within a vessel containing a bed of catalyst into a withdrawal conduit having a downward-facing catalyst entrance port, and of transferring the catalyst sample into a sample receiver located outside of the vessel which comprises the steps of:
    a. sealing the withdrawal conduit to gas flow at a point intermediate the sampling point and the sample receiver;
    b. evacuating the sample receiver and creating a pressure therein lower than that maintained in the vessel; and,
    c. rapidly unsealing the withdrawal conduit and passing a short and rapid gas flow through the withdrawal conduit, which equalizes the pressures within the vessel and the sample receiver, and effecting a fluidization of catalyst into the entrance port of the withdrawal conduit and the transfer of catalyst through the withdrawal conduit to the sample receiver.

2. The method of claim 1 further characterized in that the pressure within the sample receiver is lowered to a subatmospheric pressure.

3. The method of claim 2 further characterized in that a portion of the withdrawal conduit is evacuated.

* * * * *